United States Patent [19]
Edwards

[11] Patent Number: 6,110,196
[45] Date of Patent: Aug. 29, 2000

[54] APPARATUS AND METHOD FOR TYMPANIC MEMBRANE TIGHTENING

[76] Inventor: Stuart D. Edwards, 658 Westridge Dr., Portola Valley, Calif. 94028

[21] Appl. No.: 09/098,596

[22] Filed: Jun. 17, 1998

[51] Int. Cl.⁷ ........................................................ A61F 7/00
[52] U.S. Cl. ............................ 607/96; 607/101; 607/98; 606/32; 606/41
[58] Field of Search ..................................... 607/137, 136, 607/96, 98, 99, 100, 101, 102, 104; 606/32, 34, 41, 47, 46

[56] References Cited

U.S. PATENT DOCUMENTS

| | | | |
|---|---|---|---|
| 5,056,531 | 10/1991 | Shimoyama | 607/99 |
| 5,391,200 | 2/1995 | KenKnight et al. | 607/129 |
| 5,681,262 | 10/1997 | Isse | 600/127 |
| 5,879,348 | 3/1999 | Owens et al. | 606/41 |

*Primary Examiner*—Linda C. M. Dvorak
*Assistant Examiner*—R. Kearney

*Attorney, Agent, or Firm*—Flehr Hohbach Test; Albritton & Herbert LLP

[57] ABSTRACT

Apparatus for being held by the human hand for treating the tympanic membrane in an ear by the use of electromagnetic energy. An elongate probe has proximal and distal extremities. The proximal extremity is sized to be grasped by a human hand and the elongate probe has a length so that the distal extremity can be held in close proximity to the tympanic membrane while the proximal extremity is being held by the human hand. An energy delivery member is carried by the distal extremity. Conductors carried by the elongate probe conduct electromagnetic energy to the energy delivery member. A dispersive member is carried by the energy delivery member for dispersing the electromagnetic energy from the energy delivery member and applies energy to the tympanic membrane to heat the tympanic membrane in order to cause shrinkage of the tympanic membrane.

23 Claims, 2 Drawing Sheets

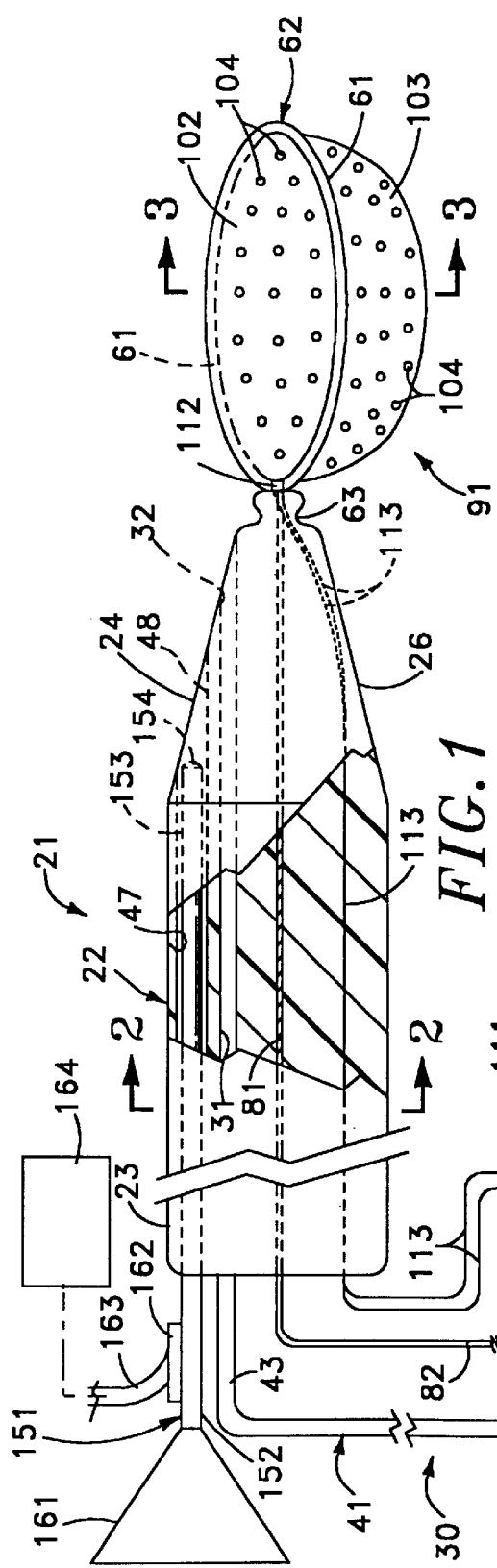
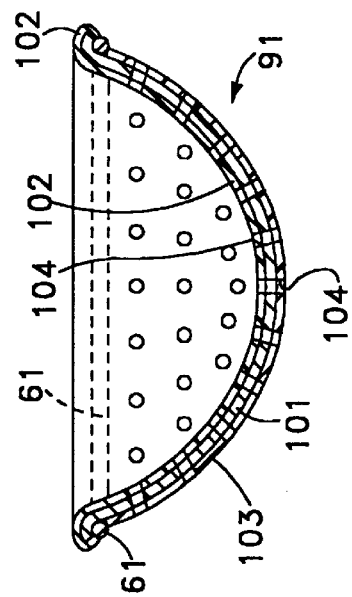
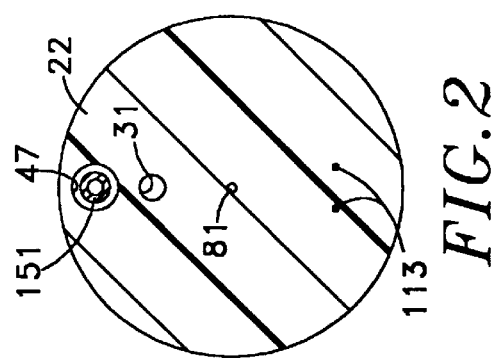

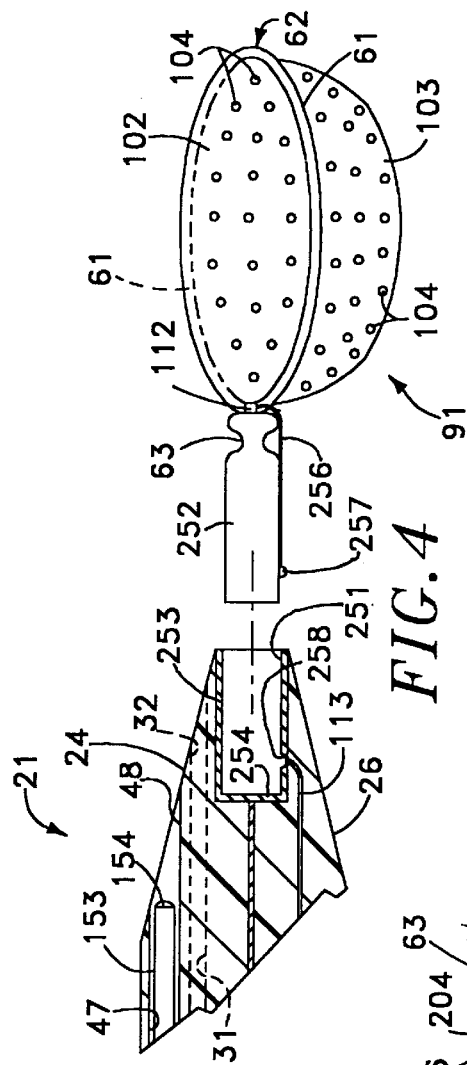
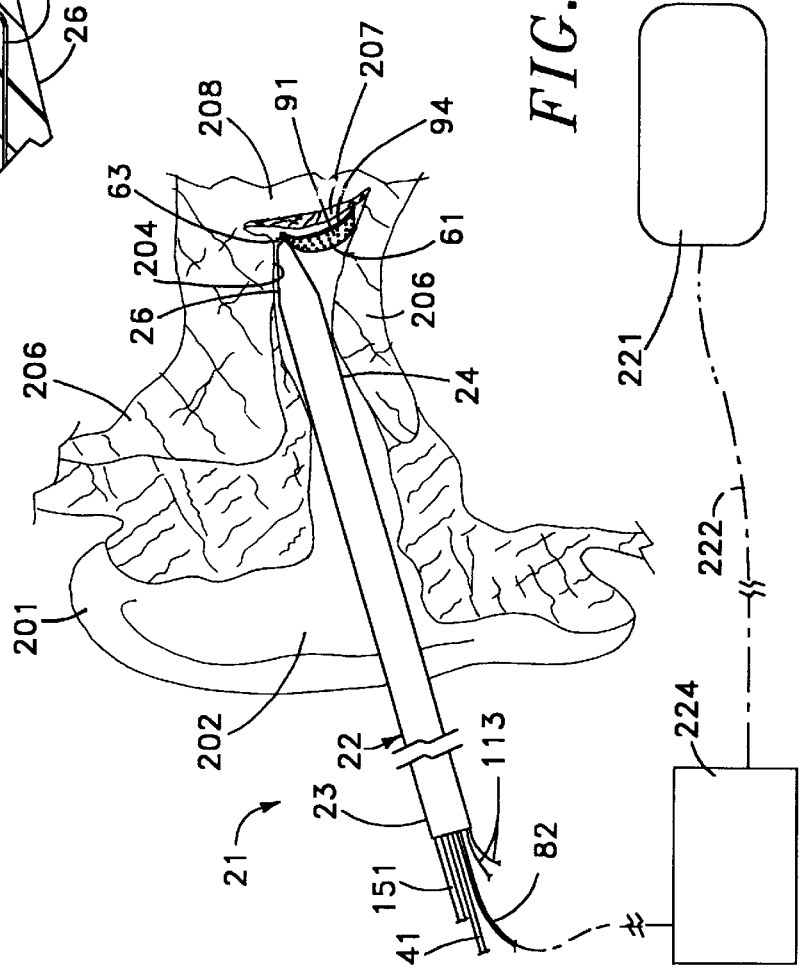
FIG. 4
FIG. 5

APPARATUS AND METHOD FOR TYMPANIC MEMBRANE TIGHTENING

This invention relates to an apparatus and method for tightening the tympanic membrane in the human ear.

The tympanic membrane of the human ear forms the border between the outer and middle ear portions of the human auditory system. As such it is an integral part of the mechanism by which sounds are conducted to the inner ear and thence the human brain. The normal tympanic membrane is taught and thin. It functions in a manner similar to the way in which the membrane on a drum functions. With infection, other disease, trauma or advancing age, the structure and function of the tympanic membrane can become compromised. The membrane can develop holes, pockets, scarring or stretching and laxity, thus impairing hearing. A significant proportion of the elderly population sustains hearing impairment due to increasing laxity of the tympanic membrane associated with aging. There is no effective remedy for this syndrome. While the tympanic membrane can be patched or even re-created in order to treat other conditions, such procedures are inappropriate for tympanic membrane laxity due to aging. Accordingly, there is a need for a device and method for tightening the tympanic membrane in such situations.

In general, it is an object of the present invention to provide a apparatus and method to tighten a lax tympanic membrane in an ear in order to restore the hearing impairment associated therewith.

Another object of the invention is to provide an apparatus and method of the above character which applies electromagnetic energy to the tympanic membrane in order to shrink and tighten said membrane.

Another object of the invention is to provide an apparatus and method of the above character which applies radio frequency energy from a radio frequency generator to the tympanic membrane in order to shrink and tighten said membrane.

Another object of the invention is to provide an apparatus and method of the above character in which means for conducting radio frequency energy from a radio frequency generator and applying said radio frequency energy to the tympanic membrane is provided in order to shrink said membrane.

Another object of the invention is to provide an apparatus and method of the above character which utilizes a loop electrode carrying a microporous member in order to conduct radio frequency energy from the electrode to the tympanic membrane.

Another object of the invention is to provide an apparatus and method of the above character which utilizes a loop electrode that is removably connectable to the apparatus.

Another object of the invention is to provide an apparatus and method of the above character in which there is provided means for delivering a conducting solution to a microporous membrane in order to apply radio frequency energy to the tympanic membrane.

Another object of the invention is to provide an apparatus and method of the above character which provides a removable and interchangeable microporous dispersive member.

Another object of the invention is to provide an apparatus and method of the above character which provides means for monitoring and controlling the amount of energy applied to the membrane by monitoring the temperature at the tympanic membrane.

Another object of the invention is to provide an apparatus and method of the above character which provides means for viewing the tympanic membrane during application of radio frequency energy to said membrane.

Another object of the invention is to provide an apparatus and method of the above character which can be easily, quickly, safely and reliably used and does not require the concomitant administration of general anesthesia.

Another object of the invention is to provide an apparatus and method of above character which is inexpensive and disposable.

Additional objects and features of the invention will appear from the following description in which the preferred embodiments and the methods using the same are described in conjunction with the accompanying drawings.

FIG. 1 is an isometric view partially in section of an apparatus for tightening the tympanic membrane incorporating the present invention.

FIG. 2 is a cross-sectional view taken along the line 2—2 of FIG. 1.

FIG. 3 is a cross-sectional view taken along the line 3—3 of FIG. 1.

FIG. 4 is an isometric view partially in section of another embodiment incorporating the apparatus of the present invention.

FIG. 5 is a frontal plan view in section depicting the human outer ear and external ear canal bordered medially by the tympanic membrane with an apparatus for tympanic membrane tightening introduced into the ear canal and positioned adjacent to the tympanic membrane to apply radio frequency energy in order to tighten the tympanic membrane.

In general the apparatus of the present invention is held by the human hand and utilizes electromagnetic energy, preferably radio frequency energy from a radio frequency generator, to tighten a lax tympanic membrane in an ear. The apparatus comprises an elongate probe having proximal and distal extremities, the proximal extremity being sized to be grasped by the human hand. The elongate probe has a length so that the distal extremity can be held in close proximity to the tympanic membrane while the proximal extremity is being held by the human hand. An energy delivery member is carried by the distal extremity and conductive means is carried by the elongate probe for conducting electromagnetic energy to the energy delivery member. There is a dispersive member carried by the energy delivery member for dispersing the electromagnetic energy from the energy delivery member and applying said energy to the tympanic membrane to heat the tympanic membrane in order to cause shrinkage of said tympanic membrane for improving hearing.

More specifically, as shown in FIGS. 1–4, the apparatus 21 of the present invention for tightening the human tympanic membrane consists of an elongate probe 22 or member formed of a suitable material such as plastic and constructed using any suitable method such as injection molding utilizing appropriate mandrels or by extrusion. The probe 22 has proximal and distal extremities 23 and 24 and is of a suitable shape, as by way of example, cylindrical or polygonal. The distal extremity 24 is provided with a tapered region 26 which may be flat, cylindrically or polygonally configured. The elongate probe 22 carries means 30 for delivering a conducting solution from the proximal extremity 23 to the distal extremity 24 as hereinafter described. The elongate probe 22 is provided with a first lumen 31 therein extending from the proximal 23 to the distal extremity 24. The first lumen 31 may be centrally disposed and is of a suitable cross-sectional shape, opening through an external exit port 32 located at the tip of the tapered region 26 of the distal extremity 24. The proximal extremity 23 of the elongate probe 22 is provided with means for adapting to and accepting a flexible tubular member 41. The flexible tubular member 41 has proximal and distal ends 42 and 43 and is provided with a lumen therein (not shown) which is in register with the first lumen 31 of the elongate probe 22. The distal end 43 of the flexible tubular member 41 may be secured to the proximal extremity 23 of the elongate probe 22 by appropriate means, such as by a suitable adhesive. The proximal end 42 of the flexible tubular member 41 is provided with an adapter or fitting, such as a female Luer fitting 44, having a lumen 46 therein in alignment with the lumen of the flexible tubular member 41 and whereby a fluid-tight seal can be maintained when solutions are introduced into the fitting 44, into the flexible tubular member 41 and thence into the first lumen 31 of the elongate probe 22 as hereinafter described.

The elongate probe 22 is provided with a second circular in cross-section viewing lumen 47 which is laterally disposed and also extends from the proximal 23 to the distal extremity 24 of the probe 22. As hereinafter discussed, the second lumen 47 has an opening 48 located laterally, along the tapered region 24 of the distal extremity 24 of the elongate probe 22 proximal to the tip of the tapered region 24 and the external port 32 of the first lumen 31.

The elongate probe 22 is of a suitable size, as for example, having a diameter ranging from 0.25" to 0.35" and a suitable length ranging from 10 to 30 cm. The first lumen 31 may have an inside diameter ranging from 0.050" to 0.150", preferably 0.075" while the second lumen 47 may have an inside diameter ranging from 0.10" to 0.20", preferably 0.15", with the opening 48 of the second lumen 47 being disposed a suitable distance proximal to the tip of the tapered portion 26 of the distal extremity 24, as for example from 1–3 cm proximally.

An energy delivery member, preferably in the form of a loop electrode 61, is secured to the tip of the tapered region 26 of the distal extremity 24 of the elongate probe 22 by suitable means as hereinafter described, adjacent to and distal of the external port 32 of the first lumen 31. The loop 62 of the electrode 61 is, preferably, elliptical in shape and, in its original configuration, extends distal to the elongate probe 22. It should be appreciated that the loop 62 may also be circular in shape as hereinafter described. The electrode 61 is constructed of a suitable wire material such as a nickel-titanium having superelastic properties so that it will return to its original configuration after being bent as hereinafter described. It should be appreciated that any suitable, flexible, conductive material such as stainless steel or titanium can also be utilized to construct the electrode 61. The electrode 61 is, preferably, secured to the distal extremity 24 of the elongate probe 22 by forming the loop 62 from a continuous wire which is embedded proximally in the elongate probe 22 as hereinafter described, thereby forming a hinge connection 63 between the electrode 61 and the distal extremity 24 of the probe 22. Alternatively, the loop electrode 61 can be a separate portion of wire secured to the distal extremity 24 of the probe 22 by a suitable adhesive, the distal extremity 24 of the probe 22 including a living hinge 63 formed during construction of the probe 22. The loop 62 is closed by appropriate means, as by of example, with solder or an appropriate adhesive.

The wire used to construct the loop electrode 61 has a suitable diameter ranging from 0.002" to 0.010". The loop 62 is sized, and can be shaped, so as to encompass an area approximating the area of the tympanic membrane, the lesser diameter ranging from 4–10 mm and the greater diameter from 8–13 mm. Various sizes and shapes of loop electrodes are provided to accommodate tympanic membranes of different shapes.

Conductive means 81 is formed by the wire 81 which is continuous with the loop electrode 61 and embedded proximally in the elongate probe 22 as hereinbefore discussed. The conductive wire 81 exits the elongate probe 22 at an appropriate location on the proximal extremity 23 thereof. The portion of wire 82 extending proximal from the proximal extremity 23 of the probe 22 is of an appropriate length so that it can be connected to a source of electromagnetic energy, preferably a radio frequency generator as hereinafter described, and the proximal end of the extending wire 82 carries an appropriate adaptor 83 therefor.

A microporous dispersive member 91 is carried by the loop electrode 61 for dispersing radio frequency energy from the electrode 61 and applying the energy substantially uniformly to the tympanic membrane as hereinafter described. The dispersive member 91 has a bag-like or sack-like conformation with a closed end 93 and an open end 93 forming a rim or annular lip 94, which is frictionally retained on the loop electrode 61. As such, dispersive members of various shapes are provided to be accommodated by loop electrodes and tympanic membranes of different configurations. The microporous member 91 includes a conductive layer 101 formed of a material capable of conducting radio frequency energy such as a metal foil. When retained on the loop electrode 61 as hereinafter described, the conductive layer 101 comes in contact with the loop electrode 61 at the rim 94 of the microporous member 91. The dispersive member 91 also includes first and second inner and outer layers 102 and 103 formed of a material that is insulative with respect to radio frequency energy, as by way of example an elastic material like latex, the outer layers 102 and 103 being disposed on opposite sides of the conductive layer 101 to create a sandwiched configuration thereof. The conductive layer 101 and first and second outer layers 102 and 103 have micropores 104 therein in registration with one another. When the apparatus of the present invention is used in conjunction with a conducting solution as hereinafter described, means 30 carried by the elongate probe 22, for delivering the solution from the proximal extremity 23 to the microporous member 91 and thence to the micropores 104, permit the solution to flow through the microporous member 91 to assist in dispersing radio frequency energy from the loop electrode 61 through said micropores 104 and applying said energy to the area of the tympanic membrane to be treated. The solution also serves to cool the surface of the tympanic membrane while the radio frequency energy is heating the same.

Means 111 for monitoring and controlling the amount of radio frequency energy applied to the tympanic membrane are provided in the form of a thermocouple 112 carried by the loop electrode 61 and insulated conductors 113 formed of an appropriate material and which extend proximally from the thermocouple 112. The conductors 113 are embedded in the elongate probe 22 during the injection molding or extrusion procedure, as hereinbefore discussed, and may be appropriately connected to the thermocouple 112, for example by being soldered. Said conductors extend out of the proximal extremity 23 of the elongate probe 22 an appropriate length so that they may be connected to a temperature monitoring device 114.

Means for viewing the tympanic membrane during application of the radio frequency energy includes the second lumen 47 and external opening thereto 48 as hereinbefore discussed. An elongate tubular member 151 having proximal and distal ends 152 and 153 is frictionally disposed in the second lumen 47. The distal end 153 has a viewing port 154, said viewing port 154 when the elongate tubular member 151 is frictionally disposed in said second lumen 47 being in register with the opening 48 in said second lumen 47. The elongate tubular member 151 is of an appropriate length and diameter so as to readily fit in the second lumen 47 as hereinbefore described. An eyepiece 161 is carried by the proximal end 152 of the elongate tubular member 151. A fitting 162 is provided on the proximal extremity 152 of the tubular member 151 and is connected to a light guide tube 163 connected into a conventional light source 164 so as to provide illumination during viewing.

Operation and use of the apparatus 21 in performing the method of the present invention may now be described in conjunction with FIGS. 1–4. The anatomy of interest is partially shown and disclosed in FIG. 4 and consists of the outer ear 201, the external ear canal 202 having proximal and distal ends 203 and 204 and surrounded by bone 206 above and below and the tympanic membrane 207 which serves as the medial border of the external ear canal 202 and separates the latter from the middle ear 208.

Let it be assumed that in anticipating use of this procedure, a patient's ear and hearing has been previously evaluated and it has been audiologically determined that the patient has a hearing deficit involving both ends of the frequency spectrum. The present procedure is most appropriate for those elderly patients in whom such a hearing deficit can be attributed to laxity of the tympanic membrane as hereinbefore discussed.

Assuming that the patient's pretreatment evaluation warrants the use of tympanic membrane tightening procedure hereinafter described, the patient can be brought into the otolaryngologist's office, an outpatient clinic or an operating room in a hospital. The patient is placed either on an operating room table or in a otolaryngology examining chair which is capable of reclining and lateral positioning. If the procedure is to be performed under general anesthesia then the necessary vital signs monitoring devices are applied to the patient and general anesthesia is induced. More commonly either no anesthesia or local anesthesia is utilized as hereinafter described. The patient's head is turned laterally so that the ear 201 to be treated is exposed and the external canal 202 of the ear 201 is substantially vertically oriented. Either before or after positioning the patient, a conventional indifferent or grounding electrode 221 is placed on the patient's upper back or upper arm so that it is adherent thereto and makes good electrical contact with the skin of the patient. If the arm is utilized it is, preferably, the arm ipsilateral to the ear 201 to be treated. The electrode 221 is connected by an electrical cable 222 into a control console 223 and radio frequency generator 224. The control console 223 is provided with a front panel 226 having appropriate digital readouts thereon. A conventional foot operated switch 227 is connected by cable 228 into the control console 223 for controlling the application of radio frequency power as hereinafter described.

Typically the elongate tubular viewing member 151, light source 164, radio frequency generator 224, temperature monitor 114 and all cables thereto are available in the aforementioned locations where the patient is to be treated and are of the reusable type. Only the elongate probe 22, electrode 61 and dispersive member 91 would be considered to be disposable after use on a single patient. Thus, in preparation for the procedure, an otoscope is utilized to re-examine the ear 201 to be treated and to re-assess the tympanic membrane 207 in order to select an elongate probe 22 with an appropriately sized and shaped loop electrode 61.

The otoscope is removed and the appropriate elongate probe 22 and electrode 61 are removed from the sterile packaging as supplied by the manufacturer. The elongate probe 22 is connected to the radio frequency generator 224 and the temperature monitor 114 by connecting the wire 82, extending from the proximal extremity 23 of the elongate probe 22, and its adaptor 83 to the cable 229 into the control console 223. The elongate tubular member 151 is inserted into the second lumen 47 of the elongate probe 22 and connected to the light source 164 as hereinbefore described and the light source 164 is turned on.

To administer local anesthesia, the physician introduces an anesthetic solution such as tetracaine or marcaine drops into the external canal 202 of the ear 201 to be treated so that the anesthetic gravitates to the tympanic membrane 207 and effects adequate anesthesia. Said anesthetic drops can also be instilled through the otoscope, positioned as hereinbefore described. After this has been accomplished, the physician may grasp the ear 201 in one hand and gently apply traction in an upward and rearward direction in order to facilitate passage of the probe 22 into the external canal 202. With his other hand the physician introduces the distal extremity 24 of the elongate probe 22 into the distal end 204 of the canal 202. Under direct vision, using the eyepiece 161 and viewing port 154 of the elongate tubular member 151, the physician carefully advances the distal extremity 24 of the elongate probe 22, with the loop electrode 61 and the dispersive microporous member 91 retained thereon, towards the tympanic membrane 207 until the electrode 61 and the dispersive member 91 contact the tympanic membrane 207. Manipulation and minimal additional advancement of the elongate probe 22 achieve optimal therapeutic positioning of the dispersive member 91 against the tympanic membrane 207, wherein the loop electrode 61 and the dispersive member 91 are flexed at the hinge connection 63 on the distal extremity 24 of the elongate probe 22 so that the electrode 61 and rim 94 of the dispersive member 91 are substantially coplanar with the tympanic membrane 207 and the closed end 92 of the dispersive member 91 uniformly covers the tympanic membrane 207. A conducting solution, such as 0.9–5% saline, preferably normal saline, is infused into the proximal extremity 23 of the elongate probe from where it travels to the dispersing member 91 and the tympanic membrane 207. This is accomplished by one of several means. The physician may simply attach a saline-filled syringe 231 to the Luer fitting 44 and intermittently inject solution into the means carried by the elongate probe 22 for delivering the solution from the proximal extremity 23 to the distal extremity 24 whence said solution exits via the exit port 32 of the first lumen 31 and enters the open end 93 of the microporous member 91, whence it flows through the micropores 104 to the tympanic membrane 207 as hereinbefore described. Alternatively, the physician may attach a conventional IV-type bag and tubing apparatus (not shown) to the Luer fitting 44 and continuously infuse a slow drip of saline to the tympanic membrane 207. A conventional battery operated or current driven fluid pump with its tubing may also be used to effect a more predictable, finer saline infusion so as not to obscure the operative field with too much fluid.

After these procedures have been accomplished, the patient is ready to have radio frequency energy supplied to the loop electrode 61, the dispersive microporous member 91 and thus, via the micropores 104, to the tympanic membrane 207. Radio frequency energy is supplied from the control console 223 and radio frequency generator 224 by operation is of the foot switch 227 by the physician. This causes radio frequency energy of the desired frequency and power level (preset by the physician) to be supplied to the loop electrode 61 and dispersive member 91 disposed adjacent to the tympanic membrane 207.

Typically, the radio frequencies can range from 300 kHz to 1 mHz although frequencies approximating 500 kHz are utilized.

The radio frequency energy is delivered at power levels ranging from 2–10 watts. The time of application of radio frequency energy can range from seconds to minutes, however, typically a period of 30 seconds to 2 minutes is appropriate. By way of example, initial power could be delivered at 3 watts for 30 seconds and thereafter adjusted to 4 watts for an additional 30 seconds and to 5 watts for the second minute of radio frequency energy application.

A slow and steady rising temperature, i.e. 5–10 degrees centigrade per minute, typically is observed during the course of treatment. The higher the power level, the faster the temperature rises. For example, at a power level of 10 watts at a frequency of 500 kHz, within 2–5 seconds a tissue temperature of approximately 80 degrees centigrade will be reached. If the temperature rises too slowly, i.e. less than 5 degrees per minute, the radio frequency power is increased by approximately 1 watt. Conversely, if the temperature rises too quickly, greater than 10 degrees centigrade per minute, the radio frequency power applied is decreased by approximately 1 watt. It should be appreciated that the radio frequency generator 224 is provided with controls which will automatically shut off the application of RF power in the event excessive temperatures (as set by the physician) are sensed by the thermocouple 112.

The use of low voltage, low frequency, low power radio frequency permits tissue volume reduction of the targeted area, the lax tympanic membrane 207, while preserving surrounding tissue and structures. In other words, by controlling the application of radio frequency energy to the tympanic membrane 207, and the resulting temperature reached at the tympanic membrane 207, the tympanic membrane 207 can be treated while preserving the integrity of the middle or inner ear 208 and surrounding structures. It is well established that human cells die as a result of being desiccated if exposed to temperatures above 47 degrees centigrade for a few seconds. Thus, the treating temperature achieved has to exceed 47 degrees. To avoid carbonization of cells however, the temperature should be maintained at less than 100 degrees centigrade. Published data confirms that an output of 8 watts during a period of six seconds will raise the tissue temperature to 55 degrees centigrade, while 10 watts applied for six seconds will raise the temperature to 82 degrees centigrade. A continuous drip of saline onto the tympanic membrane 207 through the micropores 104 helps to conduct the radio frequency energy to the tympanic membrane 207 while also serving as a buffer to prevent undue temperature rise thereat. As hereinbefore described, by monitoring the tympanic membrane 207 temperature during treatment, the thermocouple 112 on the loop electrode 61 also serves to prevent excessive tissue destruction resulting from undue heating thereof. The controlled, thermic destruction of cells forms small necrotic lesions which are absorbed within days while the adjacent tissue gently shrinks.

After terminating radio frequency application, the physician may choose to instill antibiotic drops into the treated ear. The patient is returned to a sitting position, observed for a brief period of time and thereafter permitted to leave the treatment area.

Another embodiment of the apparatus incorporating the present invention is shown in FIG. 4. It is similar to the apparatus disclosed in FIG. 1 and therefore, all similar parts of the apparatus carry the same numbers as the apparatus in FIG. 1. The embodiment shown in FIG. 4 includes an electrode 61 which is frictionally, removably connectable to the distal extremity 24 of the elongate probe 22. This is accomplished by the first lumen 31 being disposed lateral to the center of the of the elongate probe 22 with the external port 32 of the first lumen 31 therefore also being laterally disposed. In addition, instead of being laterally located, the conductive wire 81 is centrally located. The tapered region 26 of the distal extremity 24 of the elongate probe 22 is provided with a slot 251 or recess which is of a suitable configuration, as for example cylindrical, polygonal or rectangular, and has a length ranging from 0.5–7 cm, preferably approximately 2–3 cm, with a diameter ranging from 1–10 mm, preferably approximately 2.5 mm.

The loop electrode 61 includes a loop portion 62 and a shaft or stem portion 252 which shaft portion 252 is configured so as to be capable of being frictionally retained in the slot 251 of, and removably connected to, the distal extremity 24 of the elongate probe 22 as hereinafter described. The shaft portion 252 of the electrode 61 is made of a suitable material such as nickel-titanium or stainless steel and is suitably sized and configured. The loop 62 and shaft 252 portions of the electrode 61 are secured to one another by appropriate means such as by adhesive or solder joints. Preferably, the shaft 252 is constructed with a living hinge 63 situated at the distal portion of the shaft 252, immediately proximal to the point at which the shaft 252 and loop 62 portions of the electrode 61 are joined. Alternatively, the adhesive or solder joints can be constructed so as to function as a hinge connection between the loop 62 and the shaft 252.

The conductive means 81 is formed to include the loop 62 and shaft 252 portions of the electrode 61 and the slot 251 in the distal extremity 24 of the elongate probe 22 as hereinafter described. A liner 253, constructed of any suitable conductive material such as stainless steel or titanium, is retained within the slot 251 by appropriate means such as by being frictionally secured therein or adhesively bonded thereto. The liner 253 functions as a casing in which the shaft portion 252 of the electrode 61 is capable of being frictionally retained and by which conductive contact with the shaft portion 252 is established as hereinafter described. The proximal base 254 of the liner 253 is connected to the conducting wire 81 which is centrally embedded in the elongate probe 22 as hereinbefore described.

The temperature monitoring means 111 includes insulated shaft temperature conductors 256 formed of an appropriate material and sized appropriately. The shaft conductors 256 extend proximally from the thermocouple 112 and along the shaft 252 of the electrode 61 to which they are secured by appropriate means such as by an adhesive. The shaft conductors 256 may be connected to the thermocouple 112 by appropriate means, as for example by being soldered. The proximal end of the shaft conductors 256 carry pins 257 or pegs as hereinafter described.

The proximal end of the casing or liner 253 carries two holes or apertures 258 which receive the pins 257 of the shaft conductors 256 when the shaft 252 is frictionally retained in the slot 251 of the distal extremity 24 of the elongate probe 22. Elongate probe thermocouple conductors 113 are embedded in the elongate probe 22 as hereinbefore described in conjunction with the embodiment shown in FIG. 1. The distal ends of the elongate probe conductors 113 are disposed so that they terminate at the surface of the slot 251 in the tapered portion 26 of the distal extremity 24 of the elongate probe 22 thereby contacting the apertures 258 in the casing 253 when the same is retainedly secured in the slot 251 and the pins 257 on the shaft conductors 256 when the pins 257 are retained in the apertures 258 as hereinbefore described.

It should be appreciated that with this embodiment the microporous dispersive member 91 may be fixedly secured to the loop 62 of the removable electrode 61 by securing the rim 94 of the microporous member 91 to the loop 62 in any suitable manner such as by soldering or by using a suitable adhesive.

Operation and use of the apparatus shown in FIG. 4 is similar to that of the apparatus described in FIG. 1.

It should also be appreciated that other embodiments are encompassed by the apparatus of the present invention. A bi-polar radio frequency elongate probe may be constructed which comprises an active electrode carried by the distal end of the probe, a return electrode carried by the shaft of the probe and an insulated portion therebetween. During operation of such a bi-polar probe, immersion in a conductive solution permits RF current to flow from the active electrode to the return electrode, thus obviating the traditional bi-polar electrode requirement that the return electrode be in contact with the active electrode in order for current to flow. In addition, only tissue in contact with the active electrode has current pass therethrough thereby preserving other advantages of bi-polar radio frequency application. Other embodiments can include first and second lumens not extending proximally to the end of the elongate probe. Thermocouple cables can run with the conductor wire embedded in the probe. In addition, energy frequencies selected from different portions of the electromagnetic spectrum may be utilized. It should also be appreciated that collagen may be impregnated or deposited in the microporous member, thereby assisting with healing of the treated tympanic membrane. In addition, in order to achieve tight frictional retention of variously configured dispersive members by a loop electrode, said members can be soaked in saline and vacuum set on the electrode prior to being utilized in the procedure hereinbefore described.

It is apparent from the foregoing that there has been provided a novel apparatus and method for tightening and shrinking a tympanic membrane in the human ear, thus treating the same in order to improve hearing. A lax or loose tympanic membrane, or eardrum, is a common result of aging. Thus, the elderly sustain hearing loss that can be profound, especially at the lower and higher ends of the auditory spectrum. As a result of monitoring the temperature of the tympanic membrane during application of electromagnetic energy, preferably radio frequency energy, thereto and regulating the application of energy based on the temperature, membrane tissue is not burned or permanently scarred but, rather, effectively tightened and repaired in a selective and controlled manner. Hearing can be improved by as much as 10 to 20 decibels and at both ends of the auditory frequency spectrum. There is no bleeding, no requirement for general anesthesia, the procedure is brief and the potential for complications, such as pain and infection, minimal. As such, this inexpensive, easily utilized, disposable apparatus and method obviate the need for hearing aids in many elderly people.

What is claimed:

1. Apparatus for being held by the human hand for treating the tympanic membrane accessible through the external canal of the ear by the use of radio frequency energy from a radio frequency source comprising an elongate probe having proximal and distal extremities, the proximal extremity being sized to be grasped by a human hand and the elongate probe having a length so that the distal extremity can be held in close proximity to the tympanic membrane while the proximal extremity is being held by the human hand, a delivery electrode in the form of a loop lying in a plane carried by the distal extremity of the elongate probe, conductive means carried by the elongate probe for conducting radio frequency energy to said delivery electrode and a dispersive member carried by said delivery electrode for dispersing the radio frequency energy from the delivery electrode, said delivery electrode and the dispersive member carried thereby and the distal extremity of the elongate probe being sized so that the delivery electrode and its dispersive member can be delivered through the external canal of the ear to come into engagement with the tympanic membrane whereby radio frequency energy can be supplied to the tympanic membrane to cause heating of the tympanic membrane to cause tightening of said tympanic membrane.

2. An apparatus as in claim 1 wherein said delivery electrode in the form of a loop has an opening therein sized to extend over an area approximating the area of the tympanic membrane and wherein the dispersive member is secured to the loop electrode and extends over the opening to form a sock-like enclosure on one side of said opening.

3. An apparatus as in claim 2 further including means for forming a hinge connection between said delivery electrode and said distal extremity.

4. An apparatus as in claim 2 wherein said dispersive member is includes a conductive layer and a layer of insulating material in contact with the conductive layer, said conductive layer and said layer of insulating material having micropores therein in registration with each other to permit a liquid to flow therethrough.

5. An apparatus as in claim 2 wherein said dispersive member has an annular lip frictionally retained on said delivery electrode in the form of a loop.

6. Apparatus for being held by the human hand for treating the tympanic membrane in an ear by the use of electromagnetic energy comprising an elongate probe having proximal and distal extremities, the proximal extremity being sized to be grasped by a human hand and the elongate probe having a length so that the distal extremity can be held in close proximity to the tympanic membrane while the proximal extremity is being held by the human hand, an energy member carried by the distal extremity, conductive means carried by the elongate probe for conducting electromagnetic energy to said energy delivery member and a dispersive member carried by said energy delivery member for dispersing the electromagnetic energy from the energy delivery member and applying said energy to the tympanic membrane to heat the tympanic membrane in order to cause shrinkage of said tympanic membrane, said energy delivery member being an electrode secured to the distal extremity, said electrode being a loop electrode, said dispersive member being microporous, said microporous member having a bag-like conformation with a closed end and an open end forming a rim, said rim being capable of being frictionally retained on said loop electrode, said microporous member including a conductive layer formed of a material capable of conducting electromagnetic energy, said conductive layer being in contact with the loop electrode at said rim of said microporous member, first and second outer layers formed of a material that is insulative with respect to electromagnetic energy and disposed on opposite sides of the conductive layer, said conductive layer and said first and second outer layers having micropores therein in registration with one another permitting a conducting solution to flow through said microporous member to assist in dispersing the electromagnetic energy from said loop electrode through said micropores and applying said energy to the area of the tympanic membrane to be treated.

7. An apparatus as in claim 6 wherein said electromagnetic energy is radio frequency energy.

8. An apparatus as in claim 6 wherein said conductive layer is constructed of metal foil.

9. An apparatus as in claim 6 wherein said outer layers are constructed of an elastic material.

10. An apparatus as in claim 6 further including means carried by the elongate probe for delivering a conducting solution from the proximal extremity to said microporous member.

11. An apparatus as in claim 10 wherein said conducting solution delivery means includes a first lumen carried by the elongate probe, said first lumen extending from the proximal to the distal extremity of the elongate probe and having an exit port located at the distal extremity of the elongate probe and adjacent to the microporous member.

12. An apparatus as in claim 1 further including means for monitoring and controlling the amount of electromagnetic energy applied to the tympanic membrane.

13. An apparatus as in claim 12 wherein said monitoring and controlling means includes at least one thermocouple carried by said delivery electrode.

14. An apparatus as in claim 1 further including viewing means carried by the elongate Drobe for viewing the tympanic membrane as the delivery electrode is moved into engagement with the tympanic membrane.

15. An apparatus as in claim 14 wherein said viewing means includes means for illuminating the tympanic membrane during viewing.

16. An apparatus as in claim 15 wherein said viewing means includes a viewing port carried by the distal extremity of the elongate probe and an eyepiece carried by the proximal end of said elongate probe.

17. A method for treating the tympanic membrane in an ear, the ear having an external canal with proximal and distal ends, the distal end of the canal terminating adjacent to the tympanic membrane, using electromagnetic energy and an apparatus having an elongate probe being sized to be grasped by a human hand, an energy delivery member carried by the probe and a dispersive member carried by said energy delivery member for dispersing the electromagnetic energy, the method comprising introducing the elongate probe into the proximal end of the external canal, advancing said elongate probe into the distal end of the external canal so that said energy delivery member and dispersive member contact the tympanic membrane, introducing a conducting solution into the ear so that it contacts said dispersive member, supplying electromagnetic energy to said energy delivery member and dispersive member and to the tympanic membrane to heat said tympanic membrane so as to shrink and tighten the tympanic membrane to improve hearing in that ear.

18. A method as in claim 17 further including the steps of monitoring the temperature at the tympanic membrane during application of energy to the tympanic membrane and controlling the amount of energy applied to the tympanic membrane based on the temperature.

19. A method as in claim 18 wherein the temperature at the tympanic membrane is maintained within a range from 47 to 99 degrees Centigrade.

20. A method as in claim 17 further including the step of viewing the tympanic membrane during application of energy to the same.

21. A method for treating the tympanic membrane in an ear having an external canal providing access to the tympanic membrane to improve the hearing of that ear comprising delivering radio frequency energy through the external canal and into the tympanic membrane to cause heating of the tympanic membrane to cause tightening of the tympanic membrane to improve the hearing in that ear.

22. A method as in claim 21 further including the step of introducing a liquid capable of conducting radio frequency energy into the external canal of the ear into contact with the tympanic membrane while radio frequency energy is being delivered to the tympanic membrane.

23. A method as in claim 21 further including the step of sensing the temperature of the tympanic membrane to control the application of radio frequency energy to the tympanic membrane so that the tympanic membrane is maintained below a predetermined temperature.

* * * * *